US00PP32268P2

(12) United States Plant Patent

Sills et al.

(10) Patent No.: US PP32,268 P2
(45) Date of Patent: Oct. 6, 2020

(54) BLACKBERRY PLANT VARIETY NAMED 'DRISBLACKTWENTYONE'

(50) Latin Name: ***Rubus* L. subgenus *Rubus***
Varietal Denomination: DrisBlackTwentyOne

(71) Applicant: Driscoll's, Inc., Watsonville, CA (US)

(72) Inventors: Gavin R. Sills, Gilroy, CA (US); Mark F. Crusha, Capitola, CA (US); Missael Bonifacio Romero Escobedo, Ciudad Guzmán (MX)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/501,772

(22) Filed: Jun. 5, 2019

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203, 204
See application file for complete search history.

(56) References Cited

U.S. PATENT DOCUMENTS

| | | | |
|---|---|---|---|
| PP6,679 | P | 3/1989 | Moore |
| PP6,782 | P | 5/1989 | Jennings |
| PP13,525 | P3 | 1/2003 | Fear |
| PP13,758 | P3 | 5/2003 | Fear |
| PP13,759 | P3 | 5/2003 | Fear |
| PP14,682 | P3 | 4/2004 | Fear |
| PP14,765 | P2 | 5/2004 | Fear et al. |
| PP14,780 | P2 | 5/2004 | Fear et al. |
| PP15,058 | P2 | 8/2004 | Fear et al. |
| PP17,162 | P3 | 10/2006 | Clark et al. |
| PP17,983 | P2 | 9/2007 | Cabrera Avalos |
| PP22,002 | P2 | 7/2011 | Sills et al. |
| PP22,449 | P3 | 1/2012 | Clark |
| PP23,497 | P3 | 3/2013 | Clark et al. |
| PP23,725 | P3 | 7/2013 | Sills et al. |
| PP24,249 | P3 | 2/2014 | Clark |
| PP24,609 | P3 | 7/2014 | Sills et al. |
| PP24,701 | P3 | 7/2014 | Sills et al. |
| PP24,878 | P2 | 9/2014 | Sills et al. |
| PP25,502 | P3 | 5/2015 | Sills et al. |
| PP26,501 | P3 | 3/2016 | Sills et al. |
| PP26,611 | P3 | 4/2016 | Sills et al. |
| PP26,774 | P3 | 5/2016 | Sills et al. |
| PP27,129 | P2 | 9/2016 | Sills et al. |
| PP27,130 | P2 | 9/2016 | Sills et al. |
| PP27,146 | P2 | 9/2016 | Sills et al. |
| PP27,681 | P3 | 2/2017 | Sills et al. |
| PP27,746 | P3 | 3/2017 | Sills et al. |
| PP28,548 | P2 | 10/2017 | Sills et al. |
| 2016/0249505 | P1 | 8/2016 | Sills et al. |

OTHER PUBLICATIONS

Sills et al., Unpublished U.S. Appl. No. 15/932,943, filed May 24, 2018, titled "Blackberry Plant Named 'DrisBlackSeventeen'".
Sills et al., Unpublished U.S. Appl. No. 15/998,320, filed Aug. 3, 2018, titled "Blackberry Plant Variety Named 'DrisBlackEighteen'".
Sills et al., Unpublished U.S. Appl. No. 16/501,447, filed Apr. 17, 2019, titled "Blackberry Plant Variety Named 'DrisBlackTwenty'".
Sills et al., Unpublished U.S. Appl. No. 16/501,448, filed Apr. 17, 2019, titled "Blackberry Plant Variety Named 'DrisBlackNineteen'".
Voss, Donald H. "The Royal Horticultural Society Colour Chart 2001", Journal American Rhododendron Society, vol. 56, No. 1, 2002, 3 pages.
Williams et al., "DNA Polymorphisms Amplified by Arbitrary Primers are useful as Genetic Markers", Nucleic Acids Research, vol. 18, No. 22, 1990, pp. 6531-6535.

*Primary Examiner* — Susan McCormick Ewoldt
(74) *Attorney, Agent, or Firm* — Morrison & Foerster LLP

(57) ABSTRACT

A new and distinct variety of blackberry plant named 'DrisBlackTwentyOne', selected for its early production, flavor, and fruit size, is disclosed.

6 Drawing Sheets

Botanical classification: *Rubus* L. subgenus *Rubus*.

Varietal denomination: The varietal denomination of the claimed variety of blackberry plant is 'DrisBlackTwenty-One'.

BACKGROUND OF THE INVENTION

Blackberry is the common name for a multitude of plant species bearing dark purple to black aggregate fruit in the genus *Rubus* of the family Rosaceae. Most blackberries are within the subgenus *Rubus*.

Native chiefly to the northern temperate regions, blackberries are now being cultivated as a valuable fruit crop in many areas of the world, particularly in Europe, North America and Central America. Recognized for their high contents of antioxidants, dietary fiber, vitamin C, and vitamin K. Blackberry fruit are typically consumed as fresh fruit, individually quick frozen fruit, or in prepared foods, such as purees, juices, jellies, jams, grocery items, baked goods, and snack foods.

Globally, Mexico is the leading producer of blackberries, with nearly the entire crop being produced for export into the off-season fresh markets in North America and Europe. The Mexican market is almost entirely from the cultivar 'Tupi' (also spelled as 'Tupy'), In the United States, Oregon is the leading commercial blackberry producer, followed by the state of California.

Blackberries are perennial plants that typically bear biennial stems (known as "canes") from a perennial root system. The two cane types are primocanes, or first-year canes, which are usually vegetative, and floricanes, which are the same canes and produce fruit in the next growing season. In its first year, a new cane, the primocane, grows vigorously to its full length of three to six meters in a growth habit of erecting, arching, or trailing along the ground and bearing large compound leaves with 3, 5, or 7 leaflets; it does not produce any flowers. In its second year, the cane becomes a floricane and stops elongating, but the lateral buds break to produce flowering laterals that bear fruit.

Recently, primocane-fruiting blackberry varieties have been developed which are capable of flowering and fruiting on first-year canes. Primocane-fruiting blackberry varieties have several advantages, including potential of two crops on the same plant in the same year, reduction in pruning costs by mowing of canes, avoidance of winter injury, and production of fruit in an extended geographic area. However, primocane-fruiting blackberry varieties are also subject to a number of challenges, such as poor heat tolerance, lesser fruit quality, and low yield.

Blackberry is an important and valuable commercial fruit crop. Accordingly, there is a need for new varieties of blackberry plant. In particular, there is a need for improved varieties of blackberry plant that are stable, high yielding, and agronomically sound.

SUMMARY OF THE INVENTION

In order to meet these needs, the present invention is directed to an improved variety of blackberry plant. In particular, the invention relates to a new and distinct variety of blackberry plant (*Rubus* L. subgenus *Rubus*), which has been denominated as 'DrisBlackTwentyOne'.

Blackberry plant variety 'DrisBlackTwentyOne' was selected in Los Reyes, Mexico in March of 2011 and originated from a cross between the female parent blackberry plant 'DrisBlackFive' (U.S. Plant Pat. No. 24,701) and the proprietary male parent blackberry plant 'BM656.4' (unpatented). The original seedling of the new variety was first asexually propagated via root cuttings in Los Reyes, Mexico in March of 2011.

'DrisBlackTwentyOne' was subsequently asexually propagated via root cuttings, and underwent testing at a test plot in Los Reyes, Mexico from 2011 to 2019 for 8 years. The present variety has been found to be stable and reproduce true to type through successive asexual propagations via root cuttings.

'DrisBiackTwentyOne' exhibits the following distinguishing characteristics over other similar varieties when grown under normal horticultural practices in Los Reyes, Mexico:

1. Absent or very weak anthocyanin coloration on dormant cane;
2. Absent or few glandular hairs on young shoot; and
3. Medium ovate fruit shape in longitudinal section.

'DrisBlackTwentyOne' was selected for its early production, flavor, and fruit size.

BRIEF DESCRIPTION OF THE DRAWINGS

This new blackberry plant is illustrated by the accompanying photographs, which show fruit of the plant, flowers, a leaf, a cane, and a plant. The colors shown are as true as can be reasonably obtained by conventional photographic procedures. The photographs are of plants that are three years old.

DETAILED BOTANICAL DESCRIPTION

Figure 1:
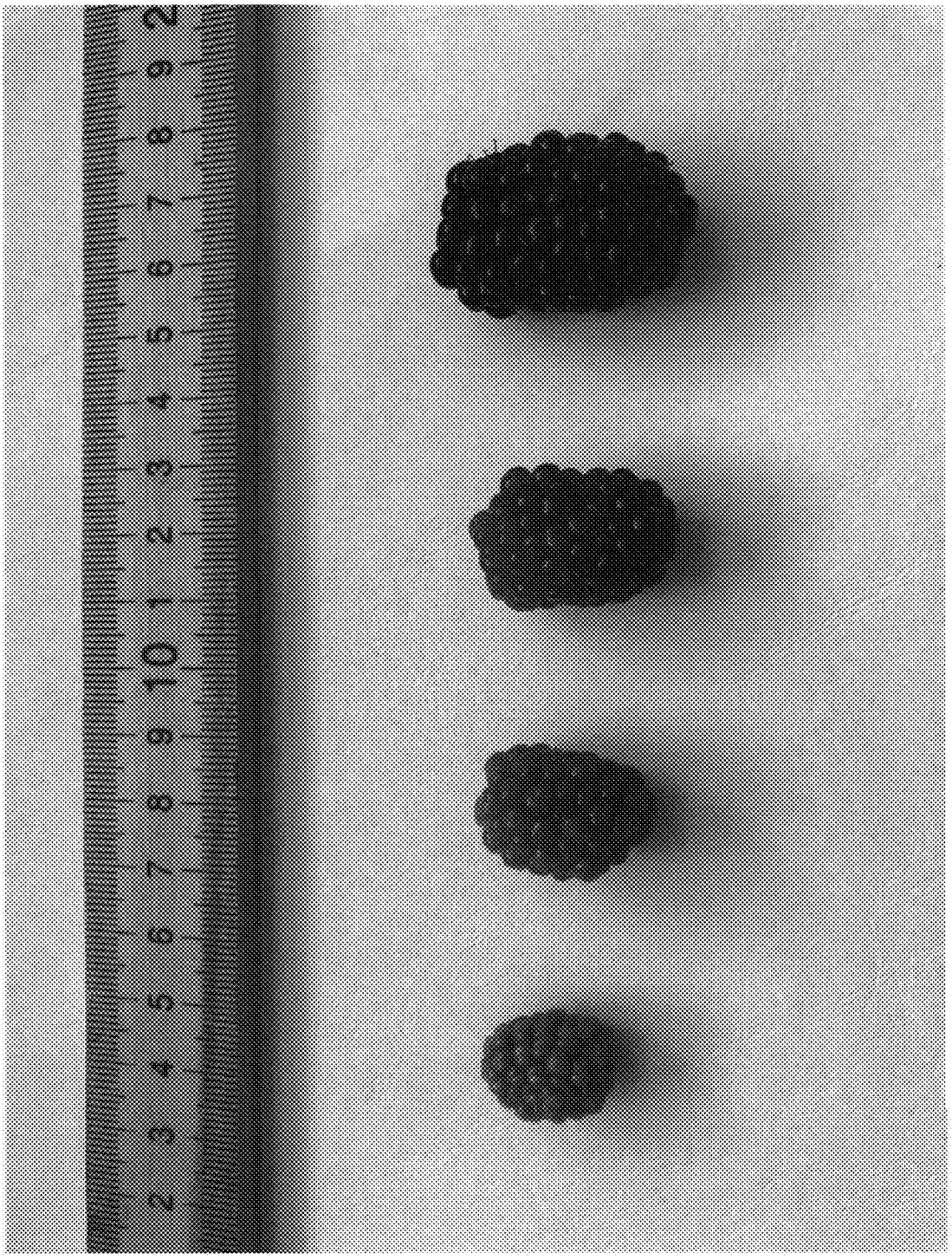
FIG. 1 illustrates typical fruit of variety 'DrisBlackTwentyOne' at various stages of development.
Figure 2:
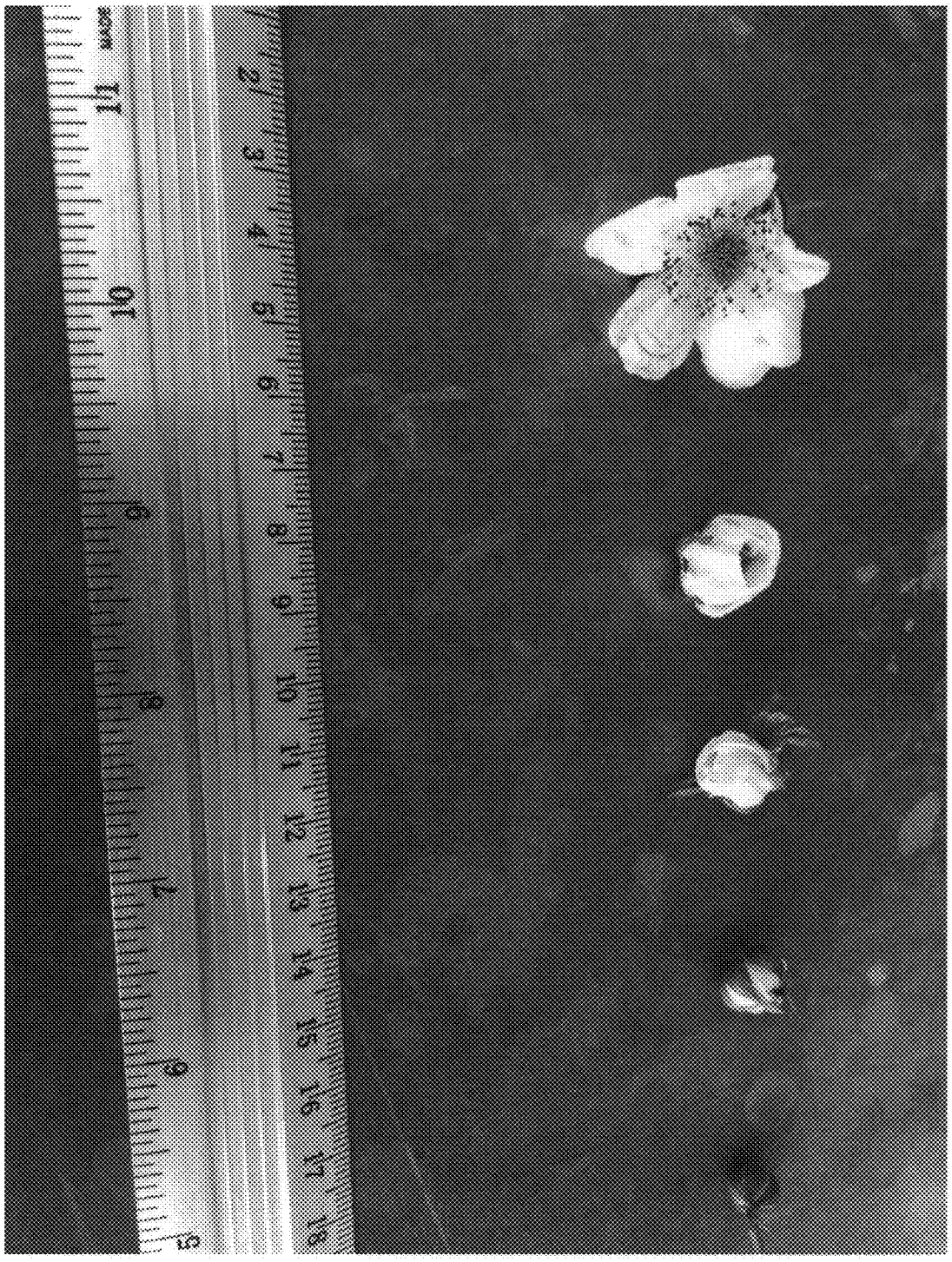
FIG. 2 illustrates typical flowers of variety 'DrisBlackTwentyOne' at various stages of development.
Figure 3:
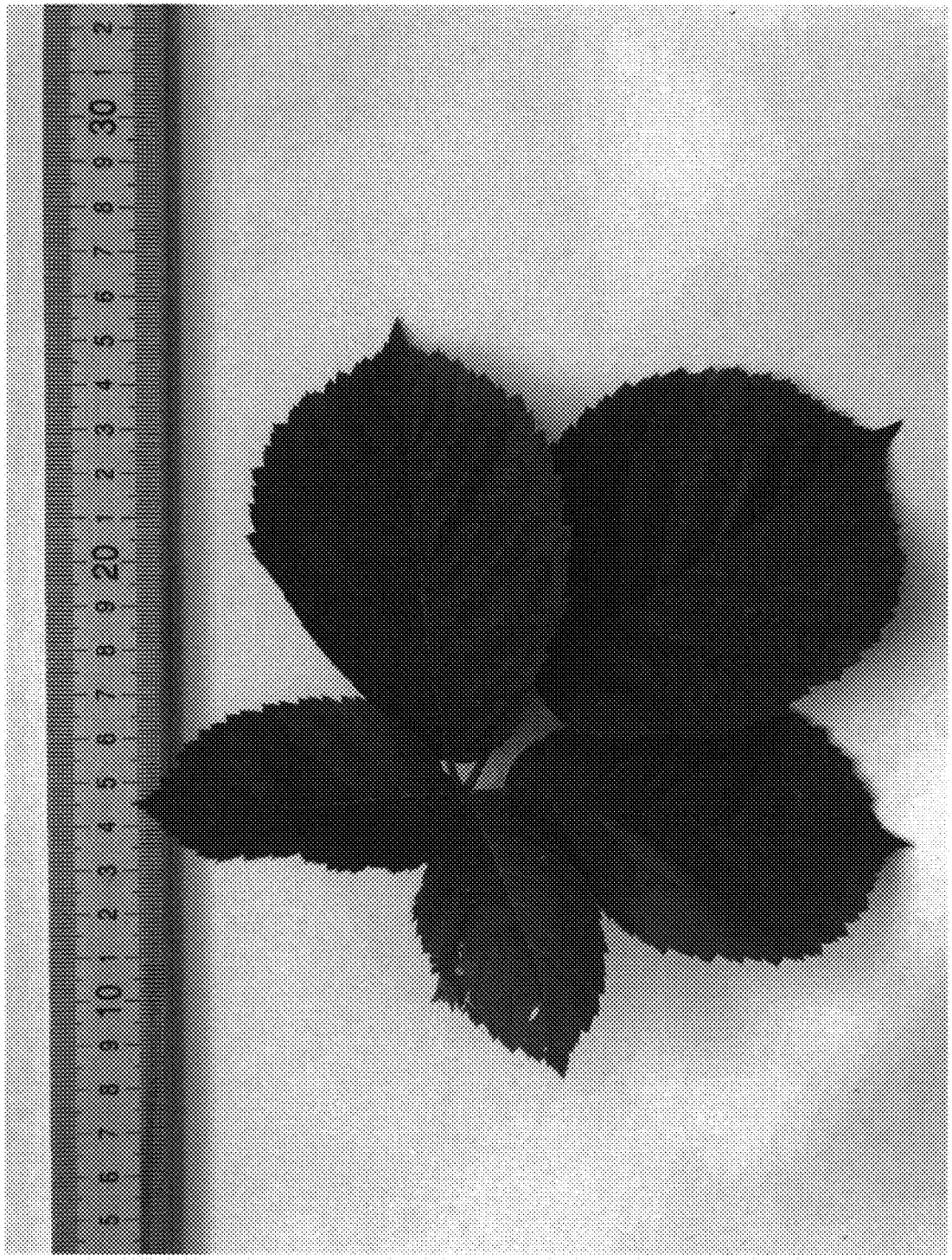
FIG. 3 illustrates a typical leaf of variety 'DrisBlackTwentyOne'.
Figure 4:
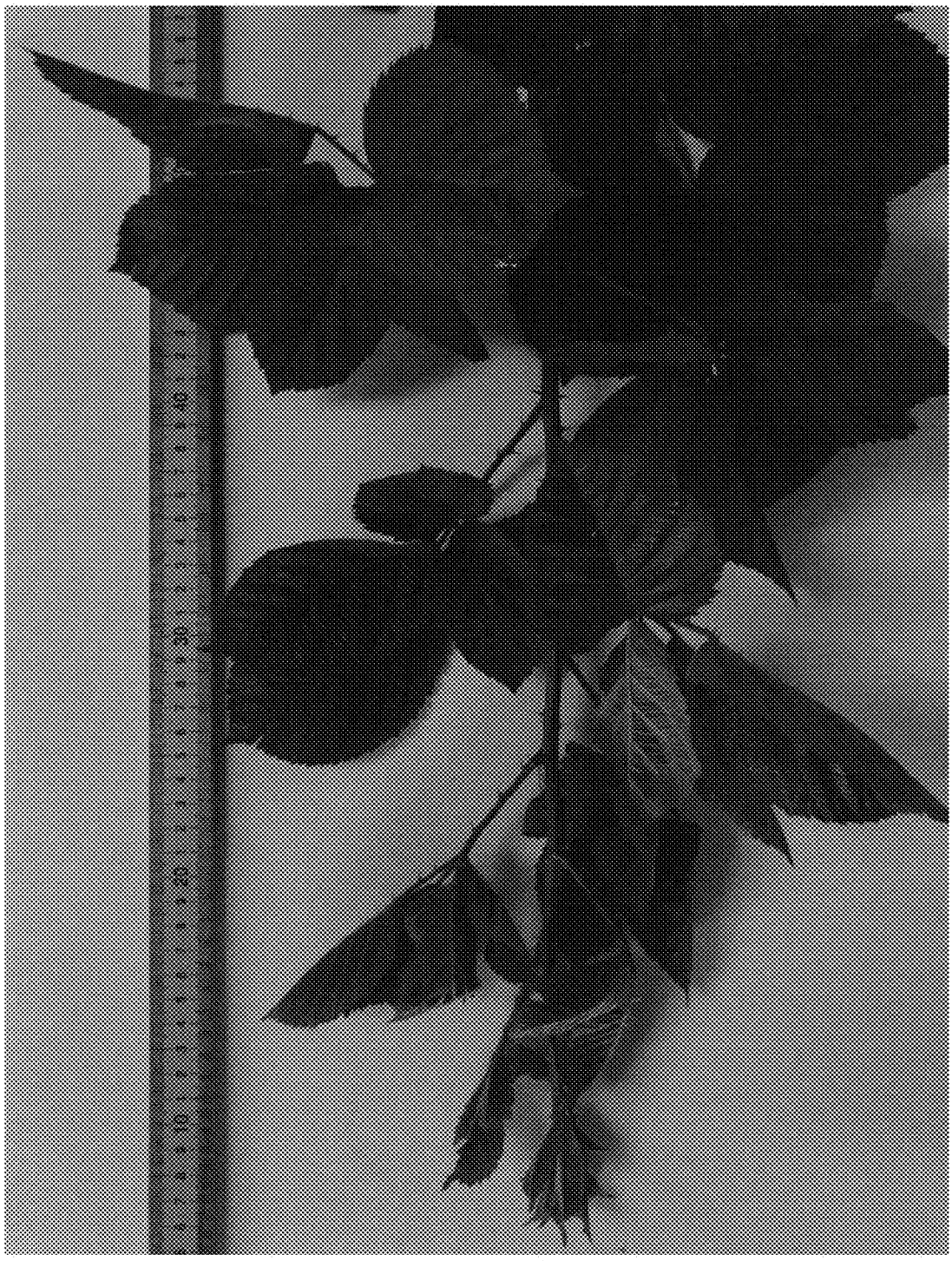
FIG. 4 illustrates a typical cane with leaves of variety 'DrisBlackTwentyOneOne'.
Figure 5:
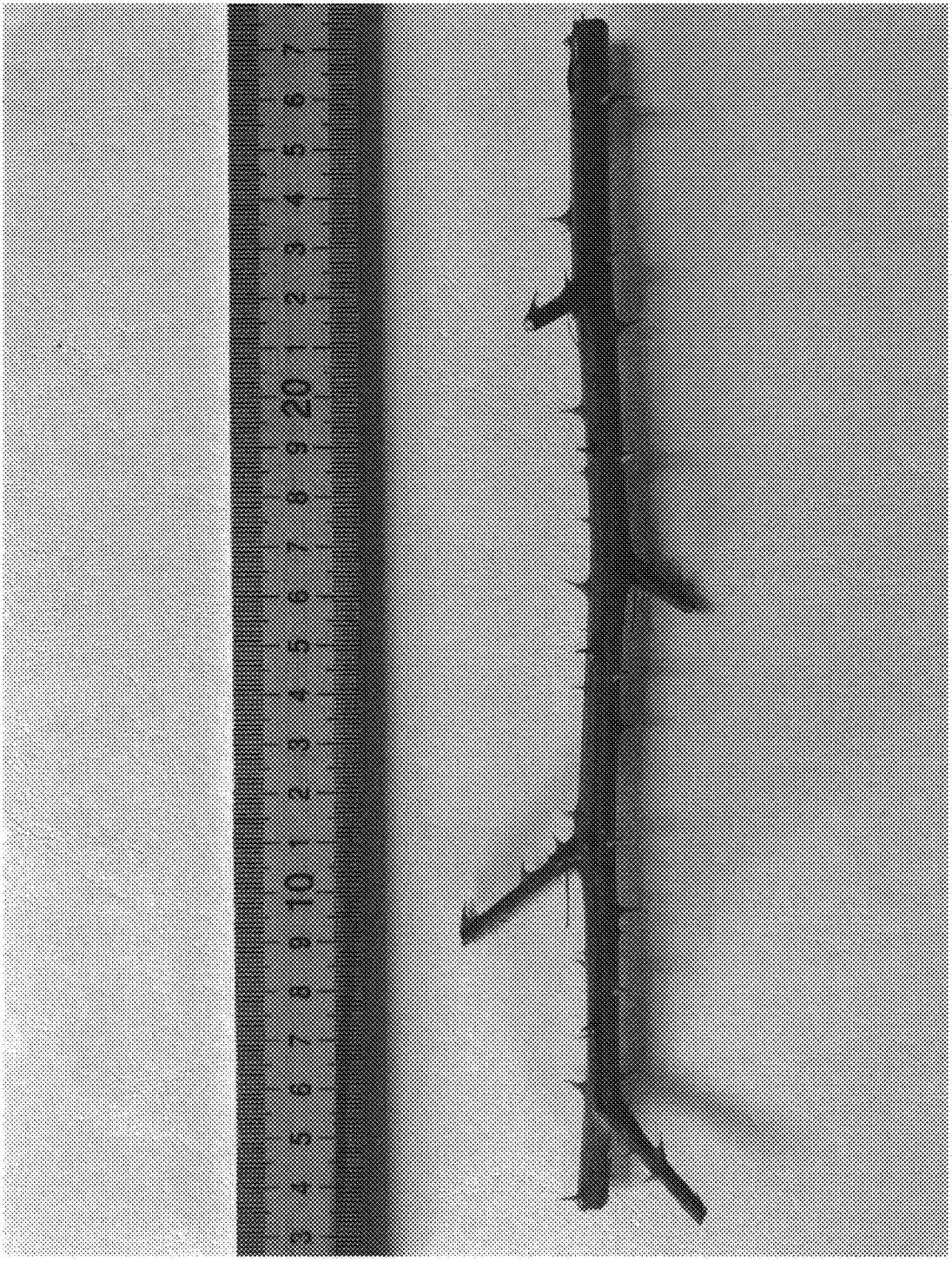
FIG. 5 illustrates a typical cane without leaves of variety 'DrisBlackTwentyOneOne'.
Figure 6:
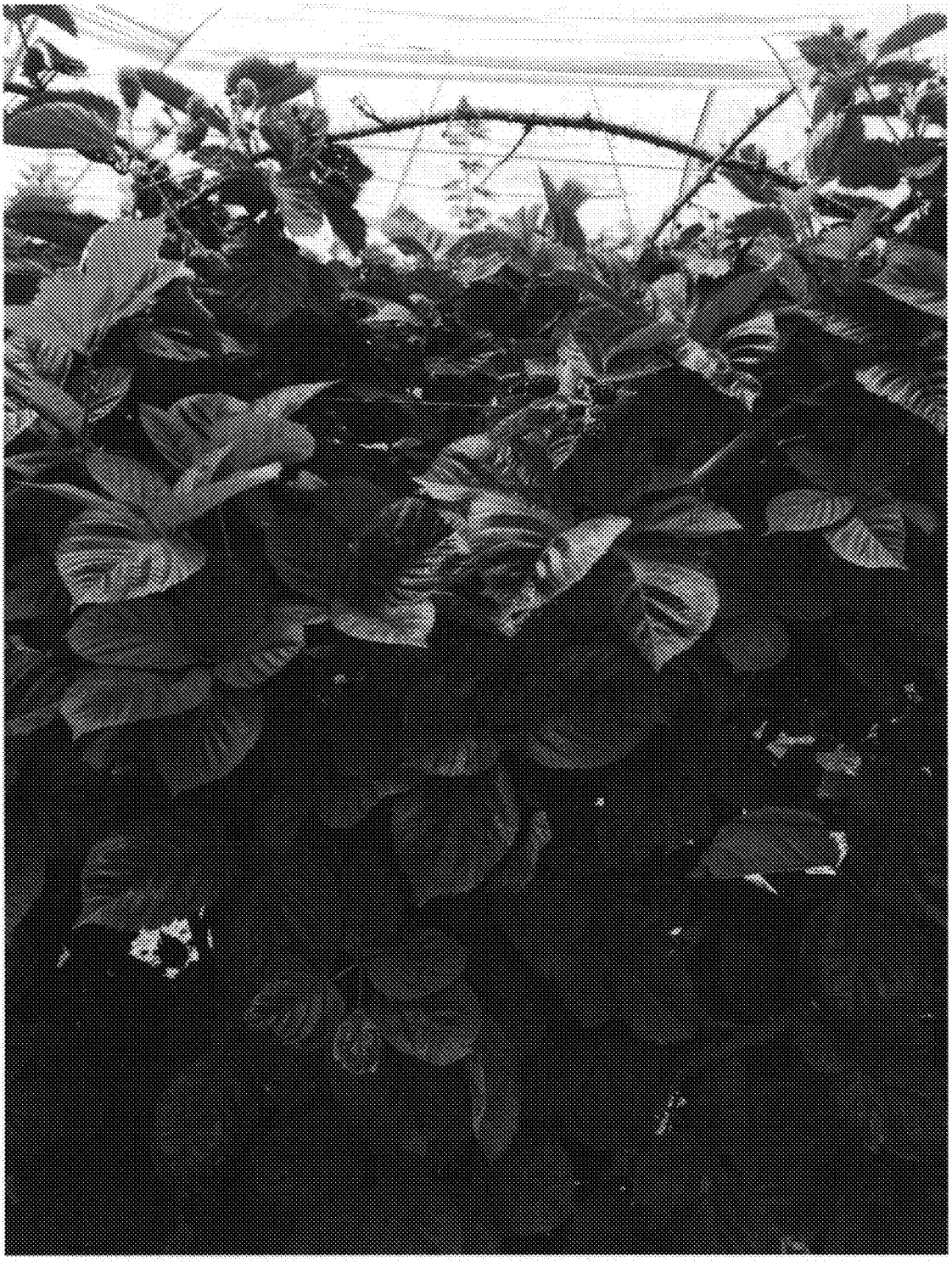
FIG. 6 illustrates a plant of variety 'DrisBlackTwentyOne'.

The following descriptions set forth the distinctive characteristics of 'DrisBlackTwentyOne'. The data that define these characteristics are based on observations taken in Los Reyes, Mexico from 2011 to 2019. This description is in accordance with UPOV terminology. Color designations, color descriptions, and other phenotypical descriptions may deviate from the stated values and descriptions depending upon variation in environmental, seasonal, climatic and cultural conditions. 'DrisBlackTwentyOne' has not been observed under all possible environmental conditions. The botanical description of 'DrisBlackTwentyOne' was taken from plants that were three years old. The indicated values represent averages calculated from measurements of several plants. Color references are primarily to The R.H.S. Colour Chart of The Royal Horticultural Society of London (R.H.S.) (2015 edition), Descriptive terminology follows the *Plant Identification Terminology, An Illustrated Glossary,* $2^{nd}$ edition by James G. Harris and Melinda Woolf Harris, unless where otherwise defined.

Classification:

*Family.*—Rosaceae.

*Botanical.*—*Rubus* L. subgenus *Rubus.*

*Common name.*—Blackberry.

*Variety name.*—'DrisBlackTwentyOne'.

Parentage:

*Female parent.*—'DrisBlackFive' (U.S. Plant Pat. No. 24,701).

*Male parent.*—'BM656.4' (unpatented).

Plant:

*Propagation.*—Root cuttings.

*Growth habit.*—Semi-upright.

Canes:

*Fruiting lateral length* ($4^{th}$ *lateral from tip*).—21.18 cm.

*Number of fruits per fruiting lateral.*—6.9.

*Internodal distance.*—4.49 cm.

*Dormant cane.*—Anthocyanin coloration: Absent or very weak. Predominant distribution of branches: Over whole length. Cross-section: Rounded to angular. Presence of spines: Present. Attitude of spine apex in relation to cane: Downwards.

Young shoots:

*Anthocyanin coloration* (*during rapid growth*).—RHS 184B (Purple).

*Intensity of green color.*—RHS 141.E (Strong bluish green).

Leaves:

*Terminal leaflet.*—Length: 85.9 mm. Width: 72.7 mm. Length/width ratio: 1.18. Lobing: Absent. Shape in cross-section: V-shaped. Undulation of margin: Strong. Shape of apex: Acute. Shape of base: Cordate.

*Lateral leaflets* (*basal pair*).—Length: 55.8 mm. Width: 42.5 mm. Length/width ratio: 1.31. Shape of apex: Acute. Shape of base: Rounded.

*Rachis length between terminal leaflet and adjacent lateral leaflets.*—26.4 mm.

*Petiole.*—Length: 55.4 mm. Diameter: 3.4 mm. Pigmentation of upper side: RHS 143A (Strong green). Pigmentation of underside: RHS 143C (Strong yellowish green).

*Leaflet.*—Type of incision of margin: Bi-serrate.

*Leaf.*—Predominant number of leaflets: 5. Type: Palmate. Intensity of green color of upper side: RHS 139A (Dark green). Intensity of green color of underside: RHS 137A (Greyish green). Texture of upper surface: Medium rough. Texture of lower surface: Soft medium. Venation pattern: Dichotomous. Vein color: RHS 145A (Strong yellow-green).

Flowers:

*Diameter.*—31.61 mm.

*Petal.*—Length: 16.40 mm. Width: 10.70 mm. Length/width ratio: 1.53. Color: RHS 155C (Pinkish white) on both upper and lower surfaces of the petal. Number of petals per flower: 5. Petal shape: Obovate. Margin: Crenate. Shape of apex: Ovate. Shape of base: Cuspidate.

*Number of flowers observed at* $3^{rd}$ *node from tip of lateral.*—3.9.

*Sepal.*—Number of sepals per flower: 5. Color of upper side: RHS 144D (Light yellow-green). Color of lower side: RHS 145B (Light yellow-green). Length: 5.41 mm. Width: 2.71 mm.

*Pedicel.*—Length: 26.82 mm. Diameter: 1.73 mm. Color: RHS 143D (Moderate yellow-green).

*Stigma.*—Length: 0.021 mm. Width: 0.019 mm. Shape: Capitate. Color: RHS 143C (Strong yellow-green).

*Style.*—Length: 1.72 mm. Width: 0.12 mm. Shape: Elongate. Color: RHS 143C (Strong yellow-green).

*Ovary.*—Length: 0.010 mm. Width: 0.08 mm. Shape: Capitate. Color: RHS 157B (Pale yellow-green).

*Stamen.*—Length: 3.6 mm. Width: 0.23 mm. Shape: Tetradynamous. Color: RHS 145C (Light yellow-green).

*Anther.*—Length: 0.90 mm. Width: 0.87 mm. Shape: Globose. Color: RHS 145C (Light yellow-green).

*Pollen.*—Diameter: 0.0004 mm. Shape: Prolate. Color: RHS 145C (Light yellow-green).

Fruit:

*Length of mature fruit.*—35.72 mm.

*Diameter of mature fruit.*—24.63 mm.

*Ratio of length to width.*—1.4.

*Average number of drupelets per fruit.*—108.

*Fruit weight.*—9.5 g/fruit.

*Soluble Solids* (*in Brix*).—15.2%.

*Titratable acidity* (*as citric acid*).—0.92%.

*Seed weight.*—0.003 g/seed.

*Shape in longitudinal section.*—Medium ovate.

*Immature fruit color.*—RHS 146A (Dark green).

*Maturing fruit color.*—RHS 185A (Deep reddish purple).

*Mature fruit color.*—RHS 202A (Black).

*Fruiting on current year's cane.*—Absent.

*Harvest interval on previous year's cane.*—Early October to mid-June.

*Yield.*—10,366 kg/hectare to 19,612 kg/hectare of fruit per season from 9-month-old plants when grown in Ciudad Guzman, Mexico.

*Market use of fruit.*—Fresh market.

*Shipping and storage characteristics.*—Following harvest, fruit can be stored for 8 days if maintained under cooled temperatures (e.g. 2° C.) that are standard for blackberry storage.

Resistance to diseases:

*Fusarium wilt* (*Fusarium oxysporum*).—Resistant.

COMPARISONS TO PARENTAL AND COMMERCIAL BLACKBERRY VARIETIES

'DrisBlackTwentyOne' differs from the female parent 'DrisBlackFive' (U.S. Plant Pat. No. 24,701) in that 'DrisBlackTwentyOne' has higher yield potential compared to 'DrisBlackFive'. Moreover, 'DrisBlackTwentyOne' differs from the female parent 'DrisBlackFive' in that 'DrisBlackTwentyOne' has absent or very weak anthocyanin coloration on dormant cane, a palmate type of leaf, and fruiting on previous year's cane only. In contrast, 'DrisBlackFive' has strong anthocyanin coloration on dormant cane, an odd-pinnate type of leaf, and fruiting on both previous year's cane and current year's cane.

'DrisBlackTwentyOne' differs from the proprietary male parent 'BM656.4' (unpatented) in that 'DrisBlackTwentyOne' is spiny while 'BM656.4' is spineless. Moreover, 'DrisBlackTwentyOne' has higher vigor than 'BM656.4'.

'DrisBlackTwentyOne' differs from commercial variety 'Tupy' (also spelled 'Tupi', unpatented) in that 'DrisBlackTwentyOne' has absent or few number of glandular hairs on young shoot, a V shape of terminal leaflet in cross-section, a medium fruit length to width ratio, and a medium ovate fruit shape in longitudinal section. In contrast, 'Tupy' has a medium number of glandular hairs on young shoot, a U shape of terminal leaflet in cross-section, a small fruit length to width ratio, and a circular to medium ovate fruit shape in longitudinal section.

'DrisBlackTwentyOne' differs from commercial variety 'DrisBlackSeventeen' (U.S. Plant Pat. No. 31,291) in that 'DrisBlackTwentyOne' has a downwards attitude of spine apex in relation to dormant cane, a predominant distribution of branches over whole length of dormant cane, absent or few number of glandular hairs on young shoot, and a very long length of fruit. In contrast, 'DrisBlackSeventeen' has an upwards attitude of spine apex in relation to dormant cane, a predominant distribution of branches only on upper half of dormant cane, many glandular hairs on young shoot, and a medium length of fruit.

What is claimed is:

1. A new and distinct variety of blackberry plant designated 'DrisBlackTwentyOne' as shown and described herein.

* * * * *